United States Patent [19]
Hartrumpf et al.

[11] Patent Number: 5,933,014
[45] Date of Patent: Aug. 3, 1999

[54] PROCESS FOR DETECTING TOTALLY OR PARTIALLY HIDDEN NON-HOMOGENEITIES BY MEANS OF MICROWAVE RADIATION

[75] Inventors: Matthias Hartrumpf; Roland Munser, both of Karlsruhe, Germany

[73] Assignee: Fraunhofer Gesellschaft zur Foerderung, Munich, Germany

[21] Appl. No.: 08/653,198

[22] Filed: May 24, 1996

Related U.S. Application Data

[63] Continuation of application No. PCT/DE94/10384, Nov. 23, 1994.

[51] Int. Cl.[6] .................................................. G01N 22/02
[52] U.S. Cl. ........................... 324/642; 324/637; 324/67
[58] Field of Search ................................... 324/632, 637, 324/638, 642, 643, 644, 646, 67; 342/459, 350, 359

[56]  References Cited

U.S. PATENT DOCUMENTS

| | | | |
|---|---|---|---|
| 3,144,601 | 8/1964 | Slabodsky | 324/642 |
| 3,534,260 | 10/1970 | Walker | 324/643 |
| 4,052,666 | 10/1977 | Fletcher et al. | 324/643 |
| 4,789,820 | 12/1988 | Parrent, Jr. et al. | 324/643 |
| 4,818,930 | 4/1989 | Flemming et al. | 324/643 |
| 4,942,363 | 7/1990 | Lowutz | 324/643 |
| 5,136,296 | 8/1992 | Poettger et al. | 342/26 |
| 5,384,543 | 1/1995 | Bible et al. | 324/637 |
| 5,497,100 | 3/1996 | Reiser et al. | 324/642 |

FOREIGN PATENT DOCUMENTS

| | | |
|---|---|---|
| 3021096A1 | 12/1981 | Germany . |
| 3922822A1 | 1/1990 | Germany . |
| 4243201A1 | 7/1993 | Germany . |
| 4208863A1 | 9/1993 | Germany . |
| A-3-235084 | 1/1992 | Japan . |

*Primary Examiner*—Diep N. Do
*Attorney, Agent, or Firm*—Evenson McKeown Edwards & Lenahan,PLLC

[57]  ABSTRACT

A process for detecting totally or partially hidden faults, such as cracks, and bubbles and the like in an opaque medium, by using microwave radiation. Microwaves from a transmitting antenna are directed against the surface of the medium which is to be inspected, and microwave radiation reflected or back scattered from the medium is detected and analyzed. In order to maximize the signal to noise ratio, minimizing the detection of radiation reflected by the surfaces of the medium itself, at least one of the transmitting antenna and the receiving antenna is oriented at an oblique angle relative to the surface of the medium.

20 Claims, 4 Drawing Sheets

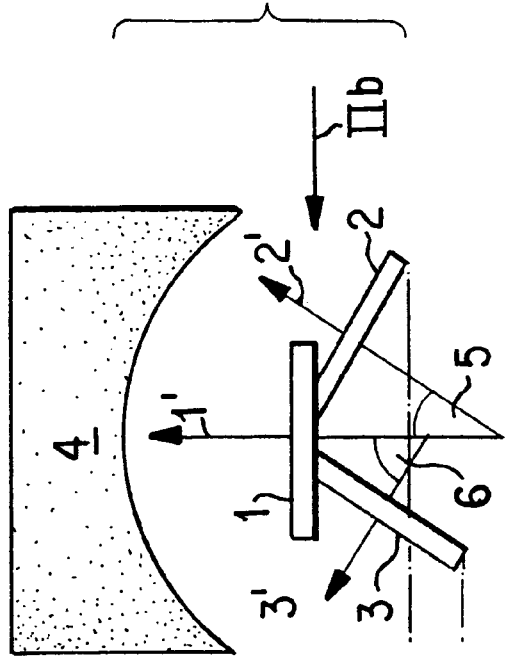
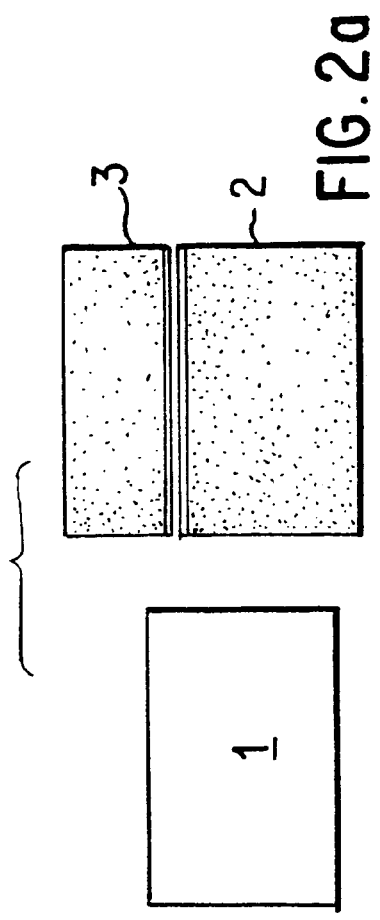
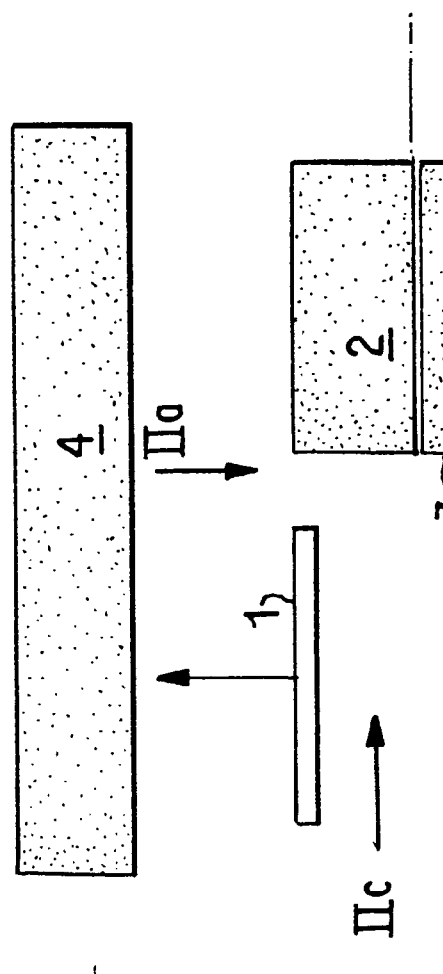

PROCESS FOR DETECTING TOTALLY OR PARTIALLY HIDDEN NON-HOMOGENEITIES BY MEANS OF MICROWAVE RADIATION

This application is a continuation of International Patent Application No. PCT/DE 94/10384, filed Nov. 23, 1994.

BACKGROUND AND SUMMARY OF THE INVENTION

The present invention relates to a process for detecting totally or partially hidden non-homogeneities (faults, such as cracks, bubbles and the like) in opaque materials, by means of microwave radiation.

Cameras are frequently used to examine inaccessible cavities such as sewage pipes for example. In this manner, the structures in the interior, such as the state of the interior wall of the pipe can be examined. In addition to the surface condition of the interior wall of the cavity, however, the adjacent surroundings may also be of interest, and in such instances, inspection by camera must be supplemented with examination by other sensors, which may be based, for example, on the reflection of microwave radiation in the surrounding medium. Therefore, special radar systems have been developed in recent years to inspect the surroundings of bore holes, including pipes from the interior.

According to the state of the art (DASA—company brochure "GeoTelKanal Tiefenradar für die Kanalinspektion" (October 1992); M. Bockmair, A: Fisch, K. Peter: "Georadar —Erkennung von Schäden und Vortriebhindernissen" ("Suchen Sehen Senieren—Internationales Symposium für Wasser/Abwasser in Lilndeu Mar. 11—13, 1993); company brochure Riooltechnieken Nederland, Schwieweg 60, 2677 AN Delft (November 1990)), these sensors consist of a pair of directional antennas (i.e., a transmitting and a receiving antenna) which are disposed side by side, and which preferably transmit and receive microwave radiation along a principal direction. These antennas are designed so that the microwave radiation is preferably transmitted or received perpendicular to the axis of the (usually cylindrical) cavity which is being inspected. In known systems, the transmitter and the receiver have hitherto been disposed along the axis of a carrier vehicle, with the axes of their directional characteristics (that is, the axes of their respective transmission or reception patterns) aligned approximately parallel to each other and perpendicular to the carrier axis (and hence, perpendicular also to the axis of the cavity). For inspection of bore holes, sensors of this type can be entered into the bore in place of a drill head. By turning the sensor about the axis of the bore hole, complete coverage of the surrounding medium can be performed.

In systems of this type, however, two different problems occur:

First, due to the alignment of the transmitting antennas approximately perpendicular to the wall of the cavity, strong reflections frequently occur at the inner and outer surfaces of the cavity wall, which reflections reach the receiving antennas directly. The intensity of the overall received radiation is highly dependent on the angle of the wall and the objects located behind it in relation to the antennas. Due to the frequency used, this dependency on the angle is much stronger than the dependency on the material or on its complex refraction index. In particular, in inspecting pipes, which usually have a moisture film on the pipe surface, the strength of the average received signal depends primarily on the geometry and alignment of the surface of the wall relative to the antennas.

Detection of the average received intensity therefore permits no conclusion concerning the state of the pipe or of the surrounding material, which must be evaluated by indirect or direct time resolution, frequency resolution or phase resolution of the received radiation by exploiting the propagation velocity of the microwave radiation (e.g. by means of frequency modulation techniques or pulse radar). However, due to the high propagation velocity, very complex, fast (and therefore very expensive) electronics are essential for inspecting the surroundings, because such components can largely suppress the signals from the interface layers (interior/pipe surface and pipe surface/homogeneous pipe surroundings), which are frequently very strong compared to the reflection that are of interest with respect to the pipe walls and surroundings.

Second, when systems of this type are used alone, the walls and/or the medium located behind it are preferably inspected in only one direction. Thus, relatively large areas of the surroundings cannot be covered without additional measures. Complete inspection, therefore, has hitherto only been realized in the case of bore holes, in which a radar sensor can be rotated instead of a drill. In this case, total coverage of the surrounding earth is possible by rotation of a pair of transmitter-receiver antennas. In prior art systems (such as, for example, pipe robots) in which the carrier vehicle does not rotate, a rotatable holding means for the antenna has to be provided if complete inspection of the surroundings is to be carried out.

The object of the present invention is to provide an inspection process of the generic type described hereinabove, which achieves improved local resolution of totally or partially hidden non-homogeneities in opaque media, by means of microwave radiation.

This and other objects and advantages are accomplished by the inspection process according to the invention, in which the antennas are aligned in such a manner that most of the radiation reflected at the (smooth) pipe wall, and at the interface between the pipe wall and the homogeneous earth, does not reach the receiving antennas as shown, for example in FIG. 1. This is achieved by inclining at least one antenna so that its average directional characteristics is at an oblique angle relative to the axis 20A of the carrier (carrier vehicle) 20 (which usually corresponds to the axis of the cavity). Hence, the microwave radiation impinges on the surface of the medium obliquely. If only one combined transmitter-receiver antenna is utilized, its directional characteristic axis must be oblique to the carrier axis 20A and therefore to the surface to be inspected (deviating from the perpendicular line by more than 5 degrees).

One advantageous embodiment of the invention utilizes a system of one transmitting antenna and a multiplicity of receiving antennas, so that the signals generated from the one transmitting antenna inside the pipe (and the surrounding medium) can be received by at least two antennas. A technically equivalent system may be composed of a multiplicity of transmitting antennas and one or a multiplicity of receiving antennas, which are not disposed one to one with the transmitting antennas. In this embodiment, the signals are generated in succession by the transmitting antennas, and are measured by the receiving antenna(s). From the different measured signals, the position of a fault is detected using known transmitting and receiving characteristics, based on the direction of the angle region defined by the directional characteristic axes of the antennas operated in the same manner. If the signals are indirectly or directly time, frequency or phase resolved, the angle position of several differently spaced faults can be detected.

With an alignment of the antenna relative to the wall of a pipe and the surrounding homogeneous earth such as described above (that is, using a single directional microwave transmitting-receiving antenna, or a multiplicity of directional microwave antennas), the radiation is reflected by the respective air/pipe and pipe/surrounding earth interfaces, back to the combined transmitting-receiving antenna or the receiving antenna, only to a small extent. Only a fault, such as a crack in the wall of the pipe, or air chamber or moisture dome in the vicinity of the pipe, scatters the radiation back to the receiver. Thus, the existence of a fault in the surrounding medium can be determined from the average received intensity, and the ratio of the "interference signal" (radiation from the wall of the medium which impinges on the receiving antenna) to the signal which is of interest (radiation reflected or scattered at faults in the pipe or the surroundings onto the receiving antenna) is considerably diminished.

In prior art antenna systems, depending on the structure of the pipe surface and its alignment in relation to the antenna, this "interference signal" can be orders of magnitude stronger than the signals from the non-homogeneities to be detected, and accordingly can be suppressed only directly or indirectly via running-time dependent effects. For this reason, it is practically impossible to detect non-homogeneities inside pipes, (that is, between the exterior and interior walls of the pipe) with the known radar processes.

Furthermore, in prior art antenna systems, the signals received from faults in the medium are also more dependent on its surface structure so that interpretation of the measured reflections is very complicated, and usually not clear. Here too, the dependency of the detected intensity on the angle of the surface relative to the antennas can be greatly reduced by means of the invented measurement of the intensity of the back scattered waves, permitting a considerably simplified and clearer interpretation of the measurements.

If manual rotation of a transmitting and receiving antenna pair is undesirable or impossible, the angular disposition of a detected dot-shaped fault relative to the antennas can be determined only by means of an arrangement of a multiplicity of transmitting and receiving antennas according to the invention, for example, in belts placed around the circumference of the carrier vehicle, which are rotated in relation to each other about the axis of the vehicle. For extensive faults, however, an average angular position (weighed with the directional characteristic of the transmitting-receiving antennas) can be detected.

In a further embodiment of the present invention, the antennas are composed of flat or curved portions. By this means in contrast to the known systems, which require a special carrier vehicle, microwave sensors or radar sensors can be set up which require very little space, and can be placed on a conventional camera inspection vehicle.

If harmonic waves of the base frequency can be emitted or received with these or other types of antennas, excited or detected sequentially by both the fundamental wave or a multiplicity of harmonic waves, the resolution of the spatial position of faults can be improved using the same system of transmitting and receiving antennas, by taking into consideration the frequency-dependent varying penetration depths of the microwave radiation and its varying transmission and reception characteristics.

Furthermore, utilizing the strength of the back scattered microwave radiation, which is dependent on the complex refraction index of the non-homogeneity at the particular frequency, the type of fault (cavity, stone, water bubbles etc.) can be accurately identified.

Moreover, even in the simplest application, in which the individual transmitting antennas are excited in succession by means of unmodulated or amplitude-modulated microwave radiation, it is possible to determine approximately, based on the different depth of penetration of the microwave radiation, the position of a fault in respect of the average radiation direction.

For total coverage of the surroundings about a given carrier vehicle, a multiplicity of transmitting and receiving antenna pairs can be disposed on the vehicle. The number of pairs of antennas is usually selected such that multiplication of the aperture angle of the transmitting or receiving characteristic by the number of antenna pairs, yields a value larger than 360°. In order to permit the simplest and best screening of the transmitter and receiver, according to the state of the art, if possible, both the transmitting antennas and the receiving antennas are disposed in the shape of a polygon, in which the radiating and receiving directions are approximately perpendicular to the axis of the carrier vehicle and its projections are parallel in pairs in a plane perpendicular to this axis, i.e. located on the carrier vehicle are one transmitting and one receiving belt respectively. Thus, complete coverage of the surrounding medium is possible; however, the angular position of detected faults in the plane perpendicular to the axis of the belt can only be accurately determined on a fraction of 360°/n.

On the other hand, much more accurate determination of the angular position compared to the state of the art is possible if, according to the invention, transmitting and receiving belts are turned in relation to each other in such a manner that radiation emitted by a transmitting antenna and scattered or reflected at the faults can be detected with at least two antennas. With the known transmitting and receiving characteristics, subsequently the angular position of the faults can be determined from the difference in the detected intensities and phases. As a rule, the same information can be determined if two transmitters emit microwave radiation in succession and the radiation scattered or reflected at the fault is detected by at least one antenna.

By placing more antenna belts on the carrier vehicle, the resolution of the spatial position of the can be further improved.

The aforedescribed processes are independent of the type of excitation and detection of the microwave radiation. The advantages are readily exploitable with very simple sensors, with CW (constant wave, with constant amplitude) or AM (amplitude modulated) excitation of an antenna or a multiplicity of antennas. With such sensors, however, a resolution in the radiation direction can only occur roughly over the overlapping regions of the transmitting and receiving characteristics or the varying range of the microwave radiation at varying frequency. If, however, additional radar techniques are utilized for excitation and temporal resolution of the received radiation, the distance of a multiplicity of faults located one behind the other in the radiation direction to the antennas can also be determined.

Other objects, advantages and novel features of the present invention will become apparent from the following detailed description of the invention when considered in conjunction with the accompanying drawings.

BRIEF DESCRIPTION OF THE DRAWINGS

FIG. 2a) is a top view of an example of a system according to the invention, while FIGS. 2b) and 2c) show side and top views respectively, of a section perpendicular to the axis of the cavity to be inspected;

DETAILED DESCRIPTION OF THE DRAWINGS

Figure 1:
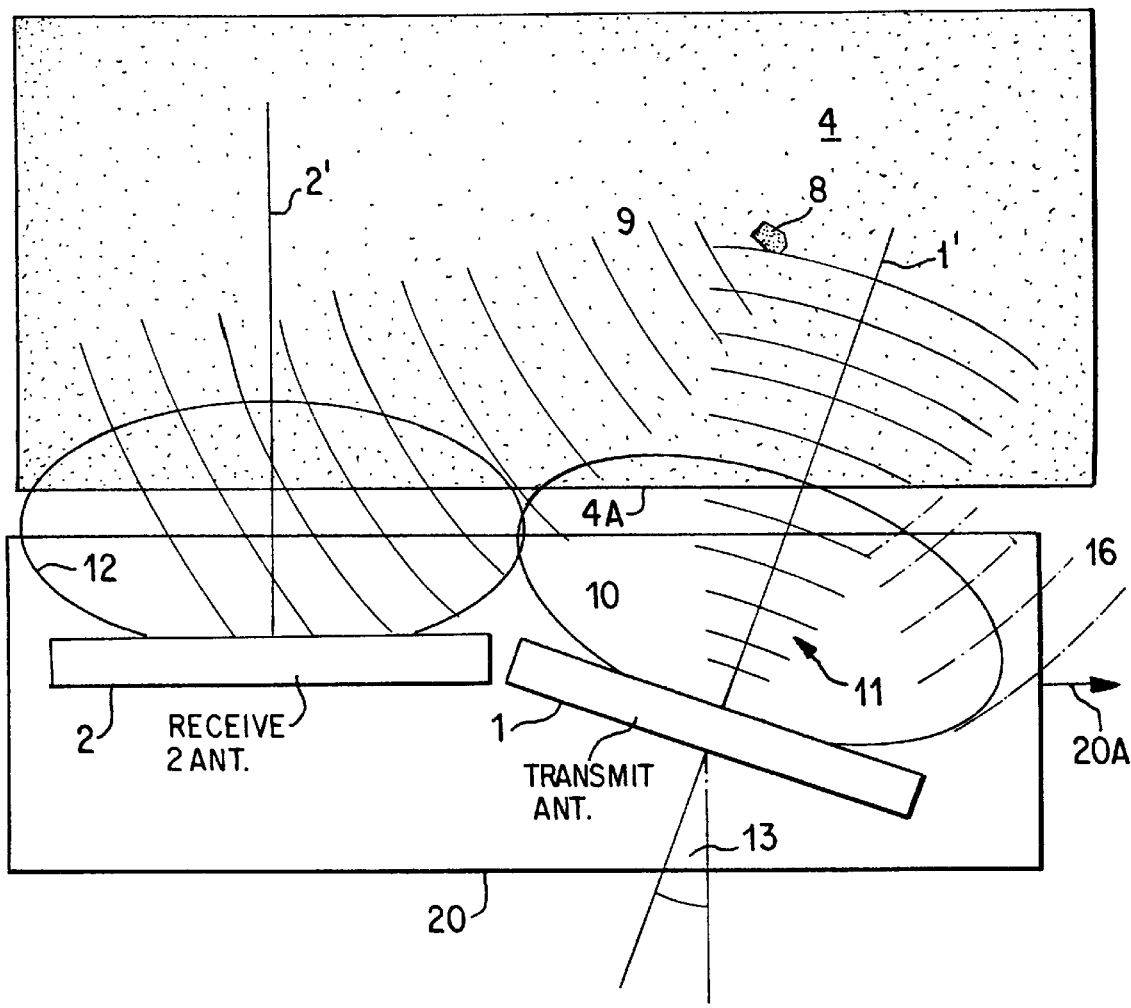
FIG. 1 is a lateral view of an example of a transmitting antenna 1 which is tilted according to the invention.

FIG. 1 shows a lateral view of an example of a transmitting antenna 1 which is tilted according to the invention, and has a radiation direction 1'. The antenna 1 is titled at an angle 13 relative to an axis which is (on average) perpendicular to the medium to be inspected. The angle 13 should be at least 13°, and preferably measure 30–60°. As shown in FIG. 1, a portion of the microwave radiation 11 emitted from this antenna (with a radiation characteristic as shown) is reflected at the interface 4A to the medium 4. The reflected radiation 16, however, is practically undetectable by the receiving antenna, because the average radiation direction 1' and the average reception direction 2' are not symmetrical with respect to the (average) perpendiculars on the medium 4 to be inspected. (That is, the line which bisects the angle formed by the transmission direction 1' and the reception direction 2' is not perpendicular to the surface of the medium.) Thus, only a few signals, which interfere with detecting non-homogeneities, can be generated at the interface to the medium. If the microwave radiation encounters a fault 8 in the medium 4, part of the radiation 9 which is back scattered therefrom is directed to the receiving antenna 2. The reference number 12 designates the directional characteristics thereof and 2' the average reception direction.

FIG. 2a) is a top view of an example of a system according to the invention, having a transmitting antenna 1 and two receiving antennas 2 and 3 for detecting the angular position of a fault in the surrounding regions of a cylindrical cavity, while FIGS. 2b) and 2c) show side and top views respectively, of a section perpendicular to the axis of the cavity to be inspected. (It should be noted that the difference in size of the two antennas is attributable to different viewing angles because of the different angular dispositions.) The microwave radiation emitted from the transmitting antenna 1 is partially scattered or reflected at the faults of the surrounding medium 4, and respective parts of the scattered radiation are detected by antennas 2 and 3. The difference between the respective detected intensities depends primarily on the distance of the fault or faults from the antennas, their position relative to the radiation, and reception characteristics of the respective antennas, as well as the angular orientation 5 or 6 of the receiving antenna 2 or 3 to the transmitting antenna 1.

Figure 3A:
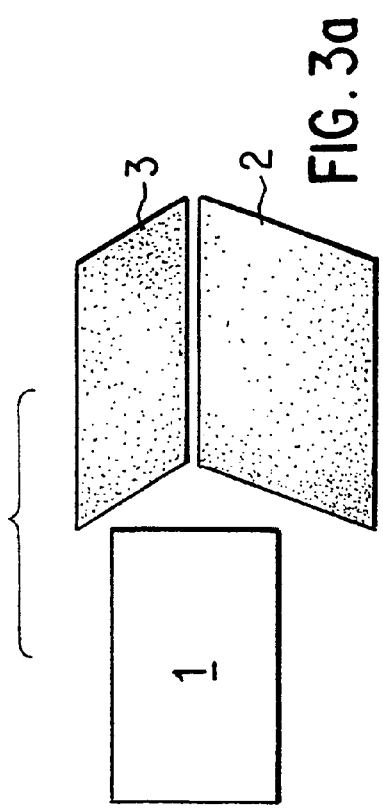
FIGS. 3a)–3c) show a system in which the antennas are oriented at an oblique angle both to the axis of the cavity being inspected, and to the wall thereof.
Figure 3B:
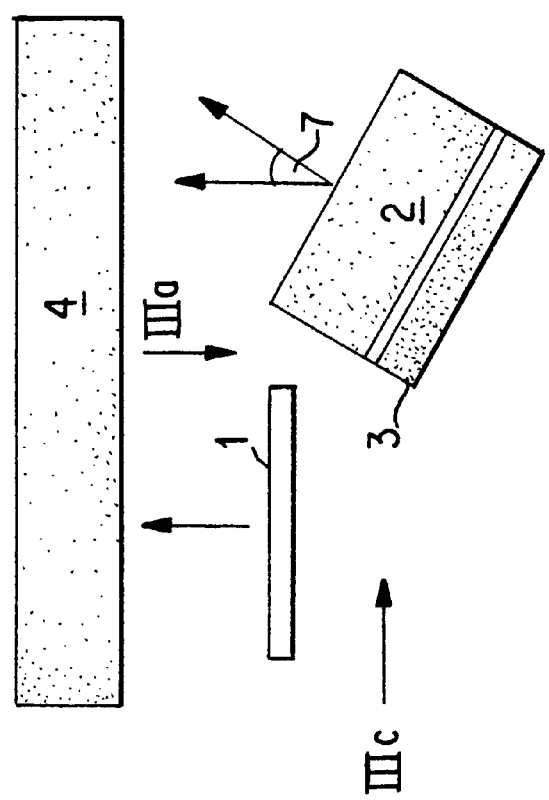
Figure 3C:
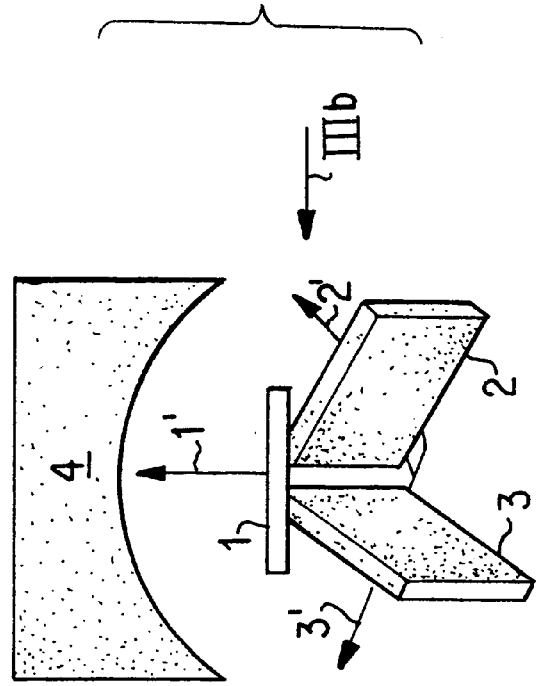

FIGS. 3a)–3c) show a system which includes both inventive concepts. In particular, FIG. 3a) shows a top view, FIG. 3b) a side view, and FIG. 3c) a top view of a section perpendicular to the axis of the cavity to be inspected. (Elements in FIG. 3 which correspond to the same elements in FIG. 2 bear the same reference numerals.) The system shown in FIG. 3 differs from the one in FIG. 2 in that the receiving antennas tilt at an angle 7 in the direction of the average radiation, relative to the longitudinal axis of the cylindrical cavity. As a result, the detection at the interface between the cavity and the surrounding medium can be avoided or minimized. Another advantage of such tilting is a reduction in sensitivity to the structure and alignment of the surface of the faults to be detected.

Figure 4:
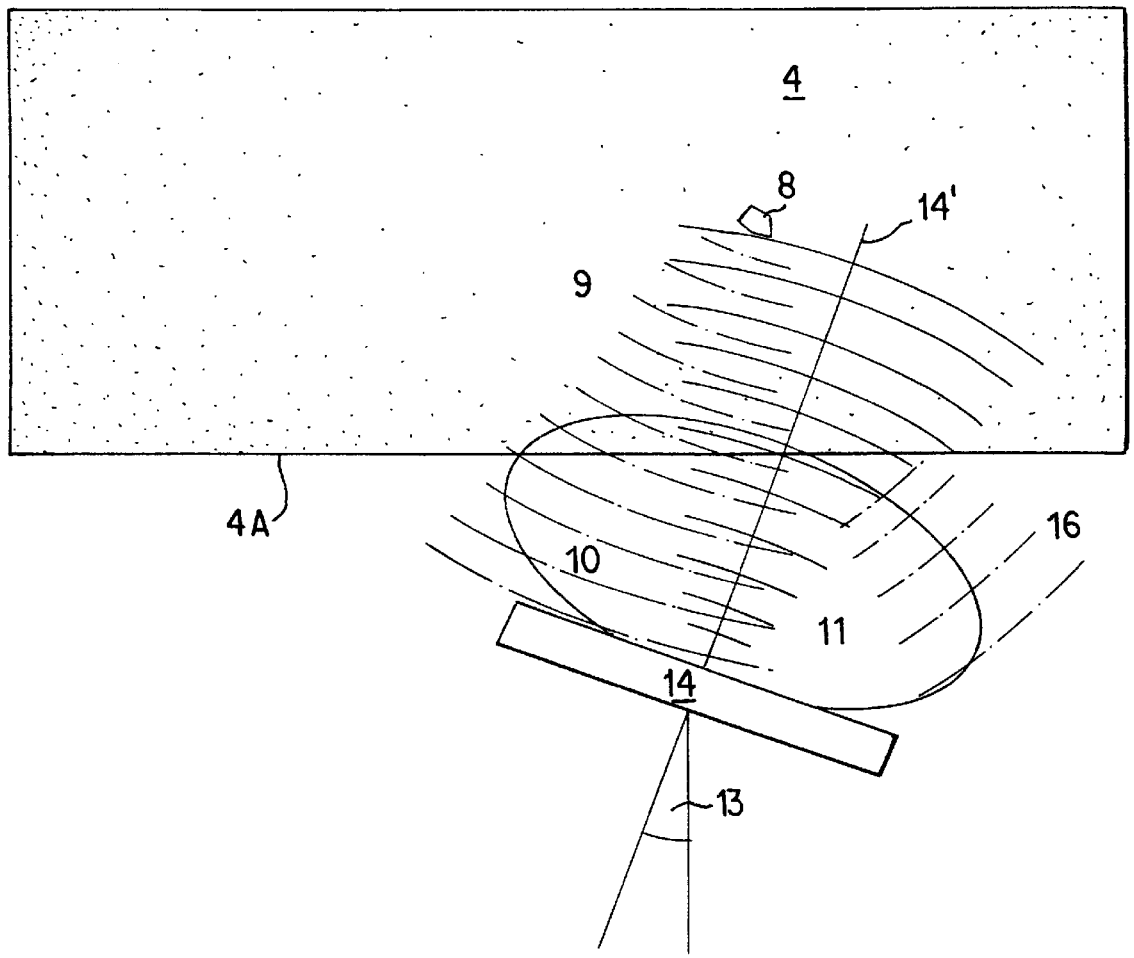
FIG. 4 shows another embodiment of the invention which uses a single directional microwave transmitting-receiving antenna.

Finally, FIG. 4 shows a system which utilizes a single directional microwave transmitting-receiving antenna 14, which according to the present invention is aligned in such a manner that the axis 14' of its directional characteristic 10 penetrates the surface 4A of the medium 4 at an oblique angle 13 (that is, other than 90°). The radiated microwaves 11 are partially reflected at the surface 4A of the medium 4. At most, a very small part of this reflected radiation 16 reaches the transmitting-receiving antenna 14, whereas the radiation 9 scattered at the fault 8 is detected by the transmitting-receiving antenna 14.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A process for detecting totally or partially hidden faults in an opaque medium by means of microwave radiation, said process comprising the steps of:

directing microwave radiation from at least one directional transmitting antenna onto a surface of said medium; and detecting microwave radiation returned from said medium, including microwave radiation scattered back by a fault in said medium, by means of at least one directional receiving antenna, said returned radiation having parameters which are indicative of at least an angular position of said fault; wherein the transmitting and receiving antennas are oriented on a carrier, with an axis of a directional characteristic of at least one of said antennas oriented at an oblique angle relative to the surface of the medium; and an axis which bisects an angle between respective axes of directional characteristics of said transmitting and receiving antennas is oriented at an oblique angle relative to the surface of the medium.

2. A process according to claim 1 wherein said at least a directional transmitting antenna and at least a directional receiving antenna comprise a plurality of pairs of transmitting and receiving antennas.

3. A process according to claim 1 wherein the orientations of said transmitting and receiving antennas are adjustable relative to said carrier and relative to each other.

4. A process according to claim 3 further comprising a plurality of additional polygonal arrangements of other transmitting and/or receiving antennas on said carrier device.

5. A process according to claim 4, wherein said step of directing microwave radiation comprises radiating microwaves in the form of one of pulses and modulated, the received radiation being determined based on one of time, frequency and phase.

6. A process according to claim 1, wherein said antennas are one of: curved and flat patch antennas.

7. A process according to claim 1 wherein said antennas are operated with a fundamental frequency and at least one harmonic frequency thereof.

8. A process according to claim 1 wherein:

the transmitting antennas are configured as an array of antennas, disposed in a first polygon arrangement about an axis of the carrier;

the receiving antennas are configured as an array of antennas, disposed in a second polygon arrangement;

average transmission and reception directions of said antennas projected in a plane perpendicular to said axis of said carrier are at oblique angles relative to one another; and the polygons are rotated relative to each other on said carrier.

9. A process according to claim 1 wherein said process comprises detecting leaking pipe connections, cracks or other damage in the wall of the pipe or air gaps or water-filled cavities, wet areas, stones, concrete, stoneware or metal objects in the vicinity of the pipes.

10. A process according to claim 1, wherein said carrier comprises an inspection/repair vehicle.

11. The process according to claim 1, wherein axes of directional characteristics of said microwave antennas are oblique to each other.

12. The process according to claim 1, wherein said at least one transmitting antenna and said receiving antenna are oriented relative to said medium such that a propagation axis of radiation transmitted by said at least one transmitting antenna and reflected from a surface of said medium is oblique to an average directional characteristic of the at least one receiving antenna.

13. The process according to claim 1, wherein said at least one transmitting antenna and said receiving antenna are oriented relative to said medium such that a propagation axis of radiation transmitted by said at least one transmitting antenna and reflected from a surface of said medium is skewed relative to an average directional characteristic of the at least one receiving antenna.

14. The process according to claim 1, wherein said propagation axis is skewed relative to an average directional characteristic of the at least one receive antenna.

15. A process for detecting faults in a medium by means of microwave radiation, said process comprising the steps of:

directing microwave radiation from at least one directional transmitting antenna onto a surface of said medium;

detecting microwave radiation returned from said medium, including microwave radiation scattered back by a fault in said medium, by means of a plurality of directional receiving antennas, said returned radiation having parameters which are indicative of at least an angular position of said fault;

wherein the at least one transmitting antenna and the plurality of receiving antennas are oriented on a carrier such that axes of directional characteristics of said receiving antennas are oblique to an axis of a directional characteristics of said at least one transmitting antenna; and determining an angular position of a fault situated within an angle formed by axes of directional characteristics of pairs of antennas, based on a parameter of the returned radiation detected by said multiplicity of directional receiving antennas.

16. A process according to claim 15 wherein an axis which bisects an angle between respective directional characteristics of said pairs of antennas is oriented at an oblique angle relative to the surface of the medium.

17. A process for detecting totally or partially hidden faults in an opaque medium by means of microwave radiation, said process comprising the steps of:

directing microwave radiation from a plurality of directional transmitting antennas onto a surface of said medium; and detecting microwave radiation returned from said medium, including microwave radiation scattered back by a fault in said medium, by means of at least one directional receiving antenna, said returned radiation having parameters which are indicative of at least an angular position of said fault; wherein said plurality of transmitting antennas and said at least a receiving antenna are oriented on a carrier such that axes of directional characteristics of said transmitting antennas are oblique to an axis of a directional characteristic of said at least one receiving antenna;

said step of directing microwave radiation onto a surface of said medium comprises transmitting microwave signals successively from each of said transmitting antennas; and an angular position of a detected fault within an angle formed by axes of directional characteristics of pairs of antennas is determined based on a parameter of the signals generated successively by the transmitting antennas and received by the at least one receiving antenna.

18. A process according to claim 17 wherein an axis which bisects an angle between respective directional characteristics of said pairs of antennas is oriented at an oblique angle relative to the surface of the medium.

19. A process for detecting faults in a medium, by means of microwave radiation, said process comprising:

directing microwave radiation from at least one direction transmitting antenna onto said medium;

detecting microwave radiation returned from said medium, including microwave radiation scattered back by a fault in said medium, by means of at least one directional receiving antenna, said returned radiation having parameters which are indicative of at least an angular position of said fault;

wherein said transmitting and receiving antennas are oriented relative to said medium such that a propagation axis of radiation from said at least one transmitting antenna reflected from a surface of said medium is oblique to an average directional characteristic of the at least one receiving antenna.

20. A process for detecting faults in a medium, by means of microwave radiation, said process comprising:

directing microwave radiation from at least one direction transmitting antenna onto said medium;

detecting microwave radiation returned from said medium, including microwave radiation scattered back by a fault in said medium, by means of at least one directional receiving antenna, said returned radiation having parameters which are indicative of at least an angular position of said fault;

wherein said transmitting and receiving antennas are oriented relative to said medium such that a propagation axis of radiation from said at least one transmitting antenna reflected from a surface of said medium is skewed relative to an average directional characteristic of the at least one receiving antenna.

* * * * *